(12) United States Patent
Folestad

(10) Patent No.: US 6,275,294 B1
(45) Date of Patent: Aug. 14, 2001

(54) ANALYZING DEVICE

(75) Inventor: Staffan Folestad, Västra Frölunda (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/308,146

(22) PCT Filed: Mar. 23, 1999

(86) PCT No.: PCT/SE99/00463

§ 371 Date: May 13, 1999

§ 102(e) Date: May 13, 1999

(87) PCT Pub. No.: WO99/49312

PCT Pub. Date: Sep. 30, 1999

(30) Foreign Application Priority Data

Mar. 23, 1998 (SE) .................................................. 9800965

(51) Int. Cl.[7] .............................. G01N 21/00; G01J 5/02
(52) U.S. Cl. ................... 356/432; 250/341.1; 250/341.7
(58) Field of Search ........................ 356/432; 250/559.07, 250/559.08, 559.46, 341.1, 341.7

(56) References Cited

U.S. PATENT DOCUMENTS 5,126,569   6/1992   Carlson .

FOREIGN PATENT DOCUMENTS

| 0767369 | 4/1997 | (EP) . |
| 0896215 | 2/1999 | (EP) . |
| 9500831 | 1/1995 | (WO) . |

OTHER PUBLICATIONS

Pharmaceutical Research, vol. 12, No. 12, 1995, pp. 2030–2035, Analysis of Drug Distribution in Hydrogels Using Fourier Transform Infrared Microscopy, Mary Tanya am Ende and Nikolaos A. Peppas.

*Primary Examiner*—Frank G. Font
*Assistant Examiner*—Amanda Merlino
(74) *Attorney, Agent, or Firm*—White & Case LLP

(57) ABSTRACT

A device for and a method of analysing a sample, comprising: a sample positioning unit (1) for positioning a sample (3); a radiation generating unit (16) for providing at least one beam of electromagnetic radiation to each of first and second surfaces of the sample (3); an imaging unit (23) for providing at least one image from radiation transmitted through each of the first and second surfaces (3a, 3b) of the sample (3); a detector unit (25) for capturing the images provided by the imaging unit (23) and generating signals corresponding thereto; and an analysing unit (61) for operating on the signals received from the detector unit (25) and generating signals representative of the three-dimensional distribution of at least one component in the sample (3).

65 Claims, 9 Drawing Sheets

ANALYZING DEVICE

The present invention relates to a device for and a method of analysing a sample, in particular a tablet, a capsule or a bulk powder.

EP-A-0767369 discloses a device for analysing a sample which performs a transmission measurement using near infra-red radiation. This device is, however, capable of providing only limited information as to the content of a sample, typically the quantity of a particular component in a sample, and cannot provide detailed information, for example, as to the three-dimensional distribution of one or more components in a sample.

It is an aim of the present invention to provide a device for and a method of analysing a sample, in particular a tablet, a capsule or a bulk powder and especially a multiple unit pellet system tablet or capsule, which is capable of providing information as to the three-dimensional distribution of one or more components in the sample.

Accordingly, the present invention provides a device for analysing a sample, comprising: a sample positioning unit for positioning a sample; a radiation generating unit for providing at least one beam of electromagnetic radiation to each of first and second surfaces of the sample; an imaging unit for providing at least one image from radiation transmitted through each of the first and second surfaces of the sample; a detector unit for capturing the images provided by the imaging unit and generating signals corresponding thereto; and an analysing unit for operating on the signals received from the detector unit and generating signals representative of the three-dimensional distribution of at least one component in the sample.

Preferably, the sample positioning unit comprises a track through which samples are in use passed.

In one embodiment the sample positioning unit is configured such that samples are moved in a stepwise manner through the track.

In another embodiment the sample positioning unit is configured such that samples are moved continuously through the track.

In one embodiment at least one of the beams of radiation is collimated.

In another embodiment at least one of the beams of radiation is converging.

In a further embodiment at least one of the beams of radiation is diverging.

In one embodiment the principal axis of at least one of the beams of radiation is substantially normal to the respective surface of the sample.

In another embodiment the principal axis of at least one of the beams of radiation is at an angle to the respective surface of the sample.

In one embodiment at least one of the beams of radiation is dimensioned to irradiate substantially entirely the respective surface of the sample.

In another embodiment at least one of the beams of radiation is dimensioned to irradiate an area smaller than that of the respective surface of the sample.

In one preferred embodiment the radiation generating unit is configured so as in use to move the at least one of the beams of radiation in at least one direction and thereby scan the at least one of the beams of radiation over substantially entirely the respective surface of the sample.

Preferably, the first and second surfaces of the sample are oppositely-directed surfaces.

Preferably, at least one of the beams of radiation is visible light.

Preferably, at least one of the beams of radiation is infra-red radiation.

More preferably, the infra-red radiation is in the near infra-red region.

Still more preferably, the infra-red radiation has a frequency in the range corresponding to wavelengths of from 700 to 1700 nm, particularly from 700 to 1300 nm.

Preferably, at least one of the beams of radiation is x-ray radiation.

Preferably, the radiation generating unit comprises at least one radiation source and at least one optical element.

Preferably, the radiation generating unit further comprises a moving diffuser downstream of each radiation source.

Preferably, the radiation generating unit further comprises a polarizer downstream of each radiation source.

In a preferred embodiment the radiation generating unit comprises first and second radiation sources and associated optical elements, each of the radiation sources providing at least one beam of radiation for irradiating respectively the first and second surfaces of the sample.

In one embodiment any or each of the radiation sources comprises a laser, preferably a diode laser.

In another embodiment any or each of the radiation sources comprises a light-emitting diode.

Preferably, the imaging unit comprises at least one optical element for providing at least one image of radiation transmitted through each of the first and second surfaces of the sample.

More preferably, the imaging unit further comprises at least one polarizer for polarizing radiation transmitted through each of the first and second surfaces of the sample.

More preferably, the imaging unit further comprises at least one beam splitter for providing a plurality of images of different single frequency or frequency band from radiation transmitted through each of the first and second surfaces of the sample.

In one embodiment the beam splitter comprises a frequency dependent beam splitter, which together with the at least one optical element provides a plurality of images of different single frequency or frequency band from radiation transmitted through each of the first and second surfaces of the sample.

In another embodiment the beam splitter comprises a non-frequency dependent beam splitter, which separates radiation transmitted through each of the first and second surfaces of the sample into a plurality of components, and a plurality of filters for filtering each of the respective components to provide radiation of different single frequency or frequency band, the beam splitter and the filters together with the at least one optical element providing a plurality of images of different single frequency or frequency band from radiation transmitted through each of the first and second surfaces of the sample.

In a further embodiment the beam splitter comprises a transmission grating, which together with the at least one optical element provides a plurality of images of different single frequency or frequency band from radiation transmitted through each of the first and second surfaces of the sample.

In a yet further embodiment the beam splitter comprises a prism array, which separates radiation transmitted through each of the first and second surfaces of the sample into a plurality of components, and a plurality of filters for filtering each of the respective components to provide radiation of different single frequency or frequency band, the prism array and the filters together with the at least one optical element providing a plurality of images of different single frequency or frequency band from radiation transmitted through each of the first and second surfaces of the sample.

In a still further embodiment the beam splitter comprises a plurality of lenses, which separate radiation transmitted through each of the first and second surfaces of the sample into a plurality of components, and a plurality of filters for filtering each of the respective components to provide radiation of different single frequency or frequency band, the lenses and the filters together with the at least one optical element providing a plurality of images of different single frequency or frequency band from radiation transmitted through each of the first and second surfaces of the sample.

Preferably, the detector unit comprises at least one detector.

In one embodiment the detector unit comprises a single detector.

In another embodiment the detector unit comprises a plurality of detectors.

In one preferred embodiment the or at least one detector is a two-dimensional array detector.

In another preferred embodiment each detector is a sub-array of an array detector.

In a further preferred embodiment the or at least one detector is a one-dimensional array detector.

In one embodiment the detector unit is configured such that in use the at least one detector is moved to capture the images provided by the imaging unit.

Preferably, the at least one detector comprises any of a CMOS chip, a CCD chip or a focal plane array.

The present invention also provides a method of analysing a sample, comprising the steps of: providing a sample; irradiating first and second surfaces of the sample each with at least one beam of electromagnetic radiation; imaging radiation transmitted through each of the first and second surfaces of the sample; capturing the imaged radiation and generating signals corresponding thereto; and operating on the signals corresponding to the imaged radiation and generating signals representative of the three-dimensional distribution of at least one component in the sample.

In one embodiment the sample is stationary during irradiation.

In another embodiment the sample is moving during irradiation.

In one embodiment at least one of the beams of radiation is collimated.

In another embodiment at least one of the beams of radiation is converging.

In a further embodiment at least one of the beams of radiation is diverging.

In one embodiment the principal axis of at least one of the beams of radiation is substantially normal to the respective surface of the sample.

In another embodiment the principal axis of at least one of the beams of radiation is at an angle to the respective surface of the sample.

In one embodiment at least one of the beams of radiation is dimensioned to irradiate substantially entirely the respective surface of the sample.

In another embodiment at least one of the beams of radiation is dimensioned to irradiate an area smaller than that of the respective surface of the sample and the respective surface of the sample is irradiated substantially entirely by scanning the at least one of the beams of radiation thereover.

In a further embodiment at least one of the beams of radiation is dimensioned to irradiate an area smaller than that of the respective surface of the sample and the respective surface of the sample is irradiated substantially entirely by moving the sample so as to scan the at is least one of the beams of radiation thereover.

Preferably, the at least one of the beams of radiation is in the form of a line.

Preferably, the first and second surfaces of the sample are oppositely-directed surfaces.

Preferably, the radiation comprises a single frequency, a single frequency band, a plurality of single frequencies or a plurality of frequency bands.

In one embodiment at least one of the beams of radiation is continuous.

In another embodiment at least one of the beams of radiation is pulsed.

Preferably, the frequency or frequency band of the radiation in each pulse is different.

Preferably, at least one of the beams of radiation is visible light.

Preferably, at least one of the beams of radiation is infra-red radiation.

More preferably, the infra-red radiation is in the near infra-red region.

Still more preferably, the infra-red radiation has a frequency in the range corresponding to wavelengths of from 700 to 1700 nm, particularly from 700 to 1300 nm.

Preferably, at least one of the beams of radiation is x-ray radiation.

Preferably, the step of imaging radiation comprises the step of providing a plurality of images of different single frequency or frequency band from radiation transmitted through each of the first and second surfaces of the sample.

A preferred embodiment of the present invention will now be described hereinbelow by way of example only with reference to the accompanying drawings, in which.

Figure 1:
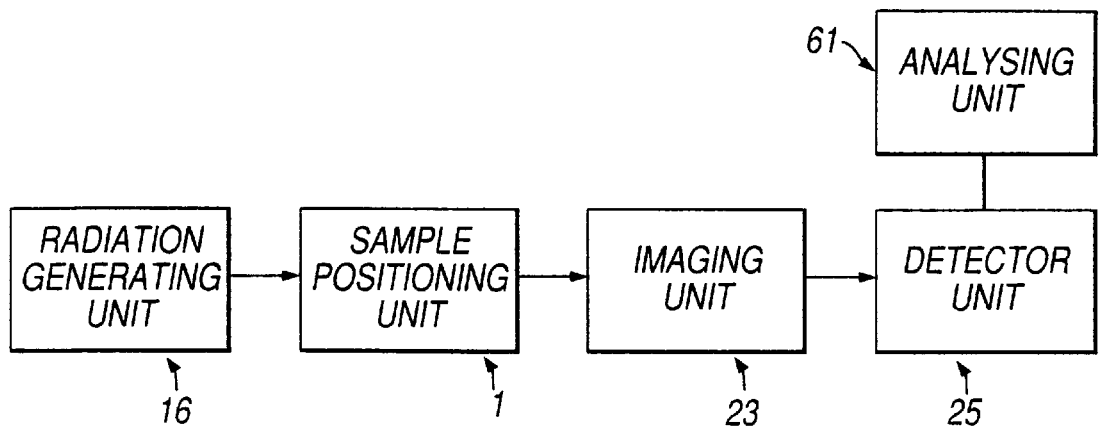
FIG. 1 illustrates schematically the elements of an analysing device in accordance with a preferred embodiment of the present invention.
Figure 2:
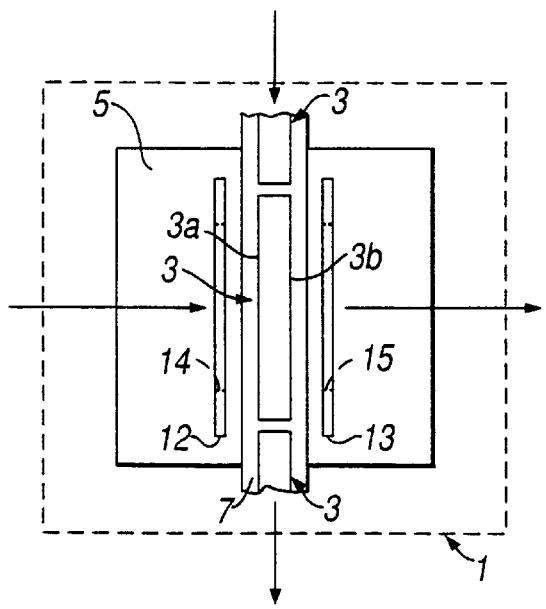
FIG. 2 illustrates schematically the sample positioning unit of the device of FIG. 1.

As illustrated in FIG. 2 the device comprises a sample positioning unit 1 for guiding a sample 3, in this embodiment a tablet or capsule, so as to position the same and present first 3a and second 3b substantially oppositely-directed surfaces thereof. The sample positioning unit 1 comprises a base 5 and a track 7, in this embodiment a tubular section formed of a material transparent to electromagnetic radiation, through which samples 3 are passed either continuously, in which case each respective sample 3 is moving during analysis, or in a stepwise manner, in which case each respective sample 3 is in turn stationary during analysis. The sample positioning unit 1 further comprises first and second shield plates 12, 13 which are disposed respectively adjacent the first and second surfaces 3a, 3b of the sample 3. The shield plates 12, 13 each include an aperture 14, 15 which defines a window through which radiation can pass. In practice, the apertures 14, 15 in the shield plates 12, 13 are sized so as to be of slightly smaller dimension than the first and second surfaces 3a, 3b of the sample 3. In this way, all radiation passing to an imaging unit 23 must pass through the apertures 14, 15 in the shield plates 12, 13 and hence the bulk of the sample 3, with the shield plates 12, 13 thus acting as a block to any radiation outside of the apertures 14, 15 therein.

The device further comprises a radiation generating unit 16 for generating electromagnetic radiation with which to irradiate the sample 3. In this embodiment the radiation generating unit 16 is configured to provide radiation having a predetermined frequency band. In a particularly preferred embodiment the radiation generating unit 16 is configured to provide radiation having a narrow frequency band, preferably in the near infra-red region. In alternative embodiments the radiation generating unit 16 can be configured to provide radiation comprising a single frequency, a plurality of single frequencies or a plurality of frequency bands, each preferably of narrow band. In addition, the radiation can be either continuous or pulsed.

Figure 3:
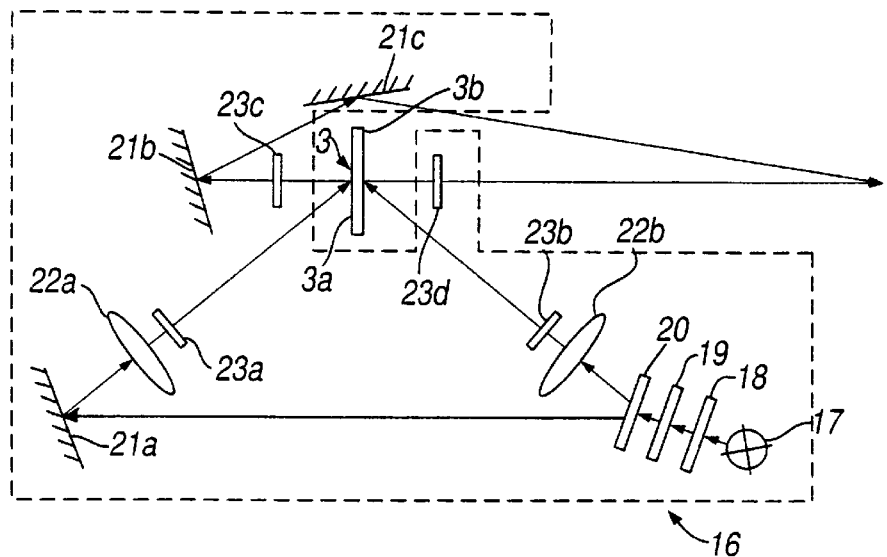
FIG. 3 illustrates schematically the radiation generating unit of the device of FIG. 1.

As illustrated in FIG. 3, the radiation generating unit 16 comprises at least one radiation source 17 and a plurality of optical elements 18, 19, 20, 21a, 21b, 21c, 22a, 22b, 23a, 23b, 23c, 23d, which include a polarizer 18, a diffuser 19, a beam splitter 20, first to third mirrors 21a, 21b, 21c, first and second lenses 22a, 22b and first to fourth shield plates 23a, 23b, 23c, 23d, that allow transmission measurements to be taken in both directions through the sample 3, that is, from the first surface 3a to the second surface 3b and vice versa, and reflectance measurements to be taken from both surfaces of the sample 3, that is, from the first and second surfaces 3a, 3b. In this embodiment the polarizer 18 is included downstream of the at least one radiation source 17 for providing completely polarized radiation. In this embodiment the diffuser 19, typically a rotating or vibrating element, is disposed downstream of the at least one radiation source 17 for preventing speckle which may occur when the at least one radiation source 17 is, for example, a laser. In a particularly preferred embodiment the radiation generating unit 16 further comprises a bundle of fibres (not illustrated) by which radiation is provided to the imaging unit 23. In particularly preferred embodiments the at least one radiation source 17 can comprise any of a source of visible light, such as an arc lamp, a source of x-rays, a laser, such as a diode laser, or a light-emitting emitting diode (LED). In a particularly preferred embodiment the radiation generating unit 16 comprises a plurality of radiation sources 17, typically a stack of light-emitting diodes or diode lasers, with which the sample 3 can be selectively irradiated. In this embodiment the radiation generating unit 16 is configured to provide beams of collimated radiation which respectively are directed at an angle to and which irradiate uniformly substantially the entire area of the first and second surfaces of the sample 3. This configuration advantageously provides, at higher angles of incidence, that, in the absence of the sample 3, radiation will not pass to the imaging unit 23 and subsequently to a detector unit 25, which could cause damage thereto. In a particularly preferred embodiment the device further comprises non-reflecting elements (not illustrated) towards which the radiation is directed when the sample 3 is not present. In an alternative embodiment the radiation generating unit 16 can be configured to provide beams of collimated radiation which are directed substantially orthogonally to the first and second surfaces 3a, 3b of the sample 3. In a further alternative embodiment the radiation generating unit 16 can be configured to provide beams of converging radiation whose point of convergence is located beyond the other of the first and second surfaces 3a, 3b of the sample 3 than to which the radiation is provided. In a yet further alternative embodiment the radiation generating unit 16 can be configured to provide beams of diverging radiation.

As will be described hereinbelow, and illustrated by FIG. 3 the at least one radiation source 17, the beam splitter 20, the mirrors 21a, 21b, 21c and the shield plates 23a, 23b, 23c, 23d are operably configured such that the detector unit 25 captures the respective transmission and reflectance images. In a first configuration, the at least one radiation source 17 provides radiation to only the first surface 3a of the sample 3 via the beam splitter 20 and the first mirror 21 a, with radiation being prevented from passing to the second surface 3b of the sample 3 by the second shield plate 23b and the radiation reflected from the first surface 3a of the sample 3 being blocked by the third shield plate 23c. In this way, the detector unit 25 is provided with an image of radiation transmitted through the sample 3 in the direction from the first surface 3a to the second surface 3b. In a second configuration, the at least one radiation source 17 provides radiation to only the first surface 3a of the sample 3 via the beam splitter 20 and the first mirror 21a, with radiation being prevented from passing to the second surface 3b of the sample 3 by the second shield plate 23b and the radiation transmitted through the sample 3 in the direction from the first surface 3a to the second surface 3b being blocked by the fourth shield plate 23d. In this way, the detector unit 25 is provided via the second and third mirrors 21b, 21c with an image of radiation reflected from the first surface 3a of the sample 3. In a third configuration, the at least one radiation source 17 provides radiation via the beam splitter 20 to only the second surface 3b of the sample 3, with radiation being prevented from passing to the first surface 3a of the sample 3 by the first shield plate 23a and the radiation reflected from the second surface 3b of the sample 3 being blocked by the fourth shield plate 23d. In this way, the detector unit 25 is provided via the second and third mirrors 21b, 21c with an image of radiation transmitted through the sample 3 in the direction from the second surface 3b to the first surface 3a. In a fourth configuration, the at least one radiation source 17 provides radiation via the beam splitter 20 to only the second surface 3b of the sample 3, with radiation being prevented from passing to the first surface 3a of the sample 3 by the first shield plate 23a and the radiation transmitted through the sample 3 in the direction from the second surface 3b to the first surface 3a being blocked by the third shield plate 23c. In this way, the detector unit 25 is provided with an image of radiation reflected from the second surface 3b of the sample 3. In use, radiation is provided selectively, preferably one of simultaneously or alternately, to the first and second surfaces 3a, 3b of the sample 3 in order for the detector unit 25 to capture the respective transmission and reflectance images.

Figure 4:
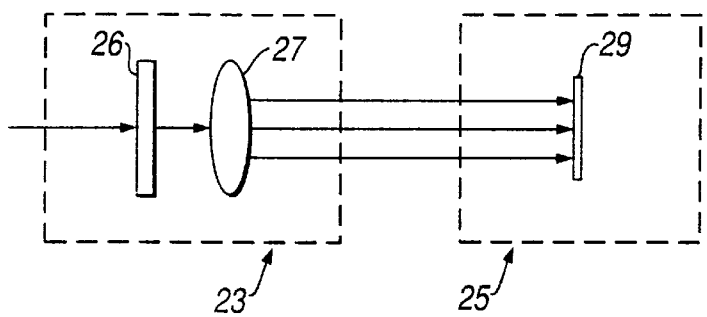
FIG. 4 illustrates schematically the imaging unit and the detector unit of the device of FIG. 1.

The device further comprises an imaging unit 23 and a detector unit 25, the imaging unit 23 providing an image of radiation received from the sample 3 to the detector unit 25. As illustrated in FIG. 4, the imaging unit 23 comprises a polarizer 26 for completely polarizing the received radiation and at least one optical element 27, in this embodiment at least one lens, and the detector unit 25 comprises at least one detector 29 for capturing the imaged radiation. In this embodiment the at least one detector 29 comprises a two-dimensional array detector, particularly a CMOS chip, a CCD chip or a focal plane array. In a particularly preferred embodiment the at least one detector 29 comprises an InGaAs camera. In a particularly preferred embodiment the imaging unit 23 further comprises a bundle of fibres (not illustrated) by which the imaged radiation is provided to the at least one detector 29. In a most preferred embodiment each discrete fibre or a group of fibres in the bundle is coupled to a separate detector 29.

In a particularly preferred embodiment, in order to provide further information as to the three-dimensional distribution of one or more components in the sample 3, the device is configured to analyse the sample 3 using radiation of a plurality of different single frequencies or frequency bands, each preferably of narrow band.

In one embodiment the radiation generating unit 16 can be configured selectively to provide radiation of different single frequency or frequency band with which the sample 3 is irradiated. In practice, this can be achieved by configuring the radiation generating unit 16 to provide pulses of radiation, each of a different single frequency or frequency band, and triggering the detector unit 25 with each pulse. In irradiating the sample 3 with radiation of each respective single frequency or frequency band the detector unit 25 receives a plurality of separate images which are then operated upon by an analysing unit 61 as will be described hereinbelow.

Figure 5:
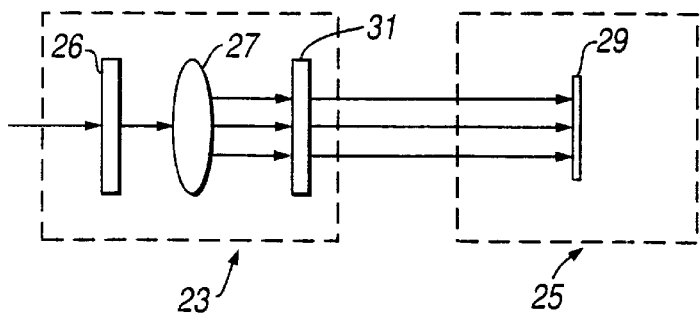
FIG. 5 illustrates schematically an alternative imaging unit for the device of FIG. 1.
Figure 6:
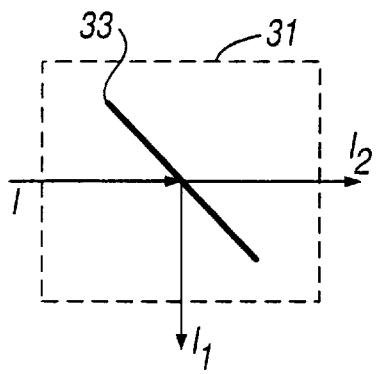
FIG. 6 illustrates schematically a first form of beam splitter for the imaging unit of FIG. 5.
Figure 7:
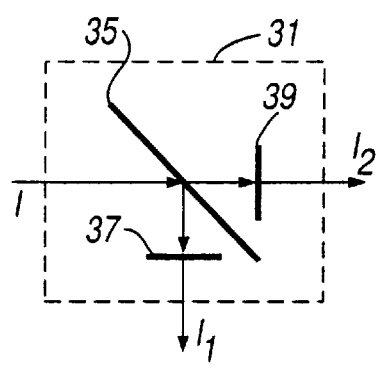
FIG. 7 illustrates schematically a second form of beam splitter for the imaging unit of FIG. 5.
Figure 8:
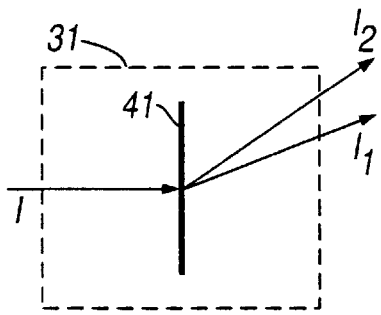
FIG. 8 illustrates schematically a third form of beam splitter for the imaging unit of FIG. 5.
Figure 9:
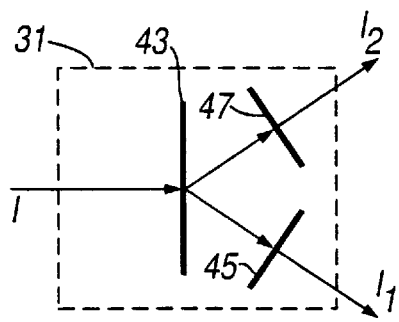
FIG. 9 illustrates schematically a fourth form of beam splitter for the imaging unit of FIG. 5.
Figure 10:
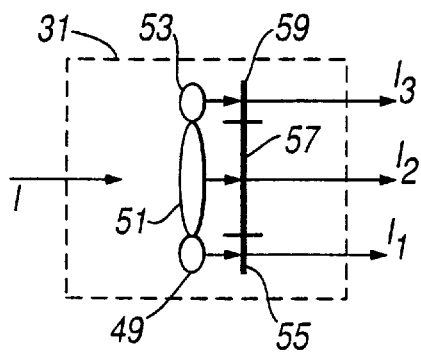
FIG. 10 illustrates schematically a fifth form of beam splitter for the imaging unit of FIG. 5.

In another embodiment, as illustrated in FIG. 5, the imaging unit 23 can further comprise a beam splitter 31 for providing two or more images of different single frequency or frequency band to the detector unit 25. Where two or more images are provided to the detector unit 25, the detector unit 25 comprises either a corresponding number of detectors 29 or a single detector 29 to which each image is provided in turn. In an embodiment where a plurality of detectors 29 are employed, the detectors 29 may be provided on a single chip having a plurality of sub-arrays which each define a detector 29. The beam splitter 31 can take many forms. In one form, as illustrated in FIG. 6, the beam splitter 31 comprises a frequency dependent beam splitter 33 which separates the image I received from the at least one lens 27 into a first image $I_1$ of a first frequency or frequency band and a second image $I_2$ of a second frequency or frequency band. In another form, as illustrated in FIG. 7, the beam splitter 31 comprises a non-frequency dependent beam splitter 35 which separates the image I received from the at least one lens 27 into two equivalent components, a first filter 37 for filtering one of the components to provide a first image $I_1$ of a first frequency or frequency band and a second filter 39 for filtering the other component to provide a second image $I_2$ of a second frequency or frequency band. In a further form, as illustrated in FIG. 8, the beam splitter 31 comprises a transmission grating 41 which separates the image I received from the at least one lens 27 into a first image $I_1$ of a first frequency or frequency band and a second image $I_2$ of a second frequency or frequency band. In a yet further form, as illustrated in FIG. 9, the beam splitter 31 comprises a prism array 43 which separates the image I received from the at least one lens 27 into two equivalent components, a first filter 45 for filtering one of the components to provide a first image $I_1$ of a first frequency or frequency band and a second filter 47 for filtering the other component to provide a second image $I_2$ of a second frequency or frequency band. In a still yet further form, as illustrated in FIG. 10, the beam splitter 31 comprises first, second and third lenses 49, 51, 53 which respectively separate the image I received from the at least one lens 27 into first, second and third equivalent components, a first filter 55 for filtering the first component to provide a first image $I_1$ of a first frequency or frequency band, a second filter 57 for filtering the second component to provide a second image $I_2$ of a second frequency or frequency band and a third filter 59 for filtering the third component to provide a third image 13 of a third frequency or frequency band.

Figure 11:
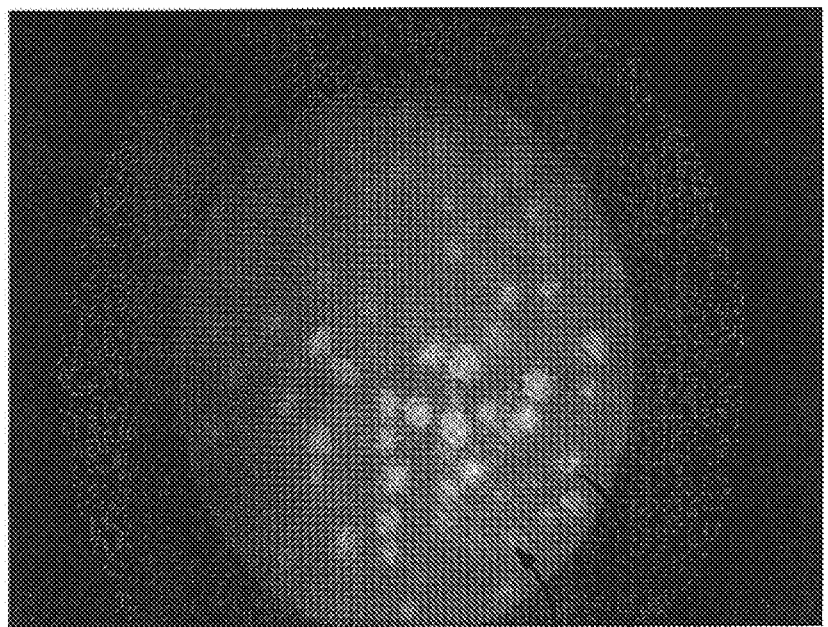
FIG. 11 illustrates an image generated by the analysing unit of radiation transmitted through the first surface of a first sample.
Figure 12:
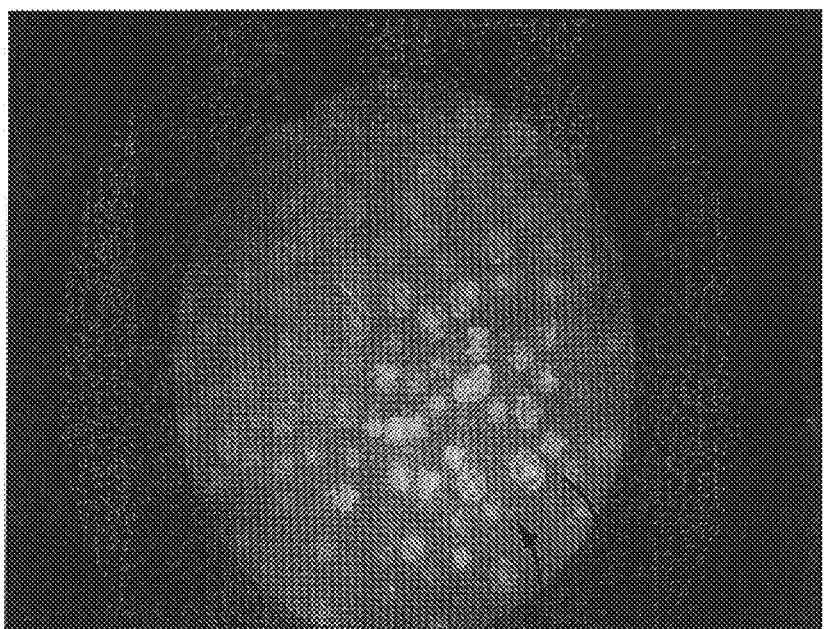
FIG. 12 illustrates an image generated by the analysing unit of radiation transmitted through the second surface of the first sample.
Figure 13:
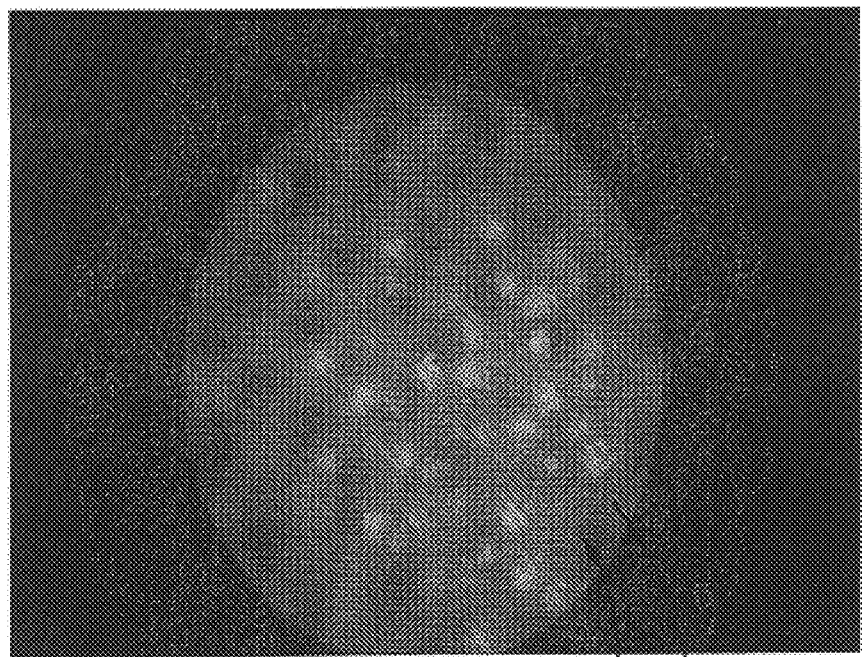
FIG. 13 illustrates an image generated by the analysing unit of radiation transmitted through the first surface of a second sample.
Figure 14:
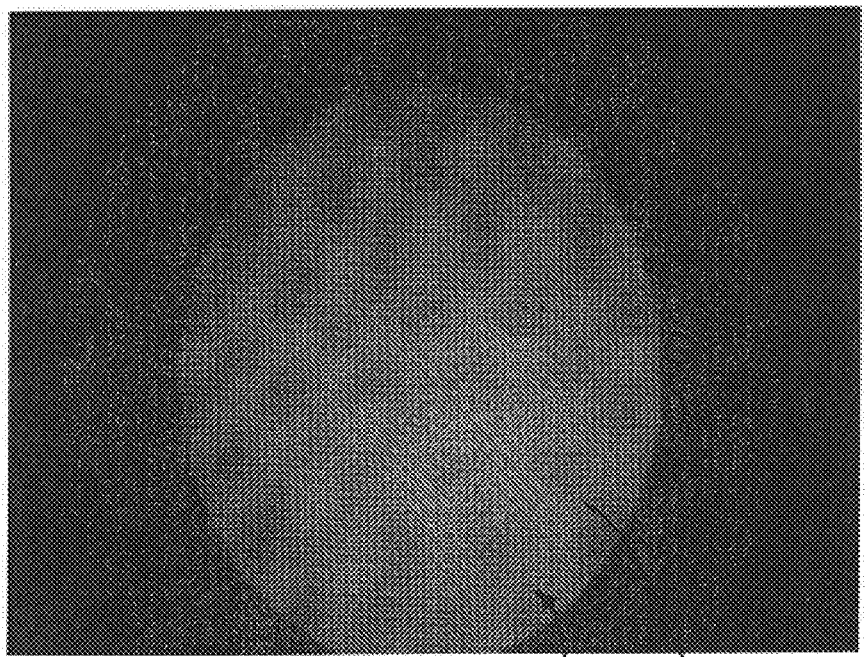
FIG. 14 illustrates an image generated by the analysing unit of radiation transmitted through the second surface of the second sample.
Figure 15:
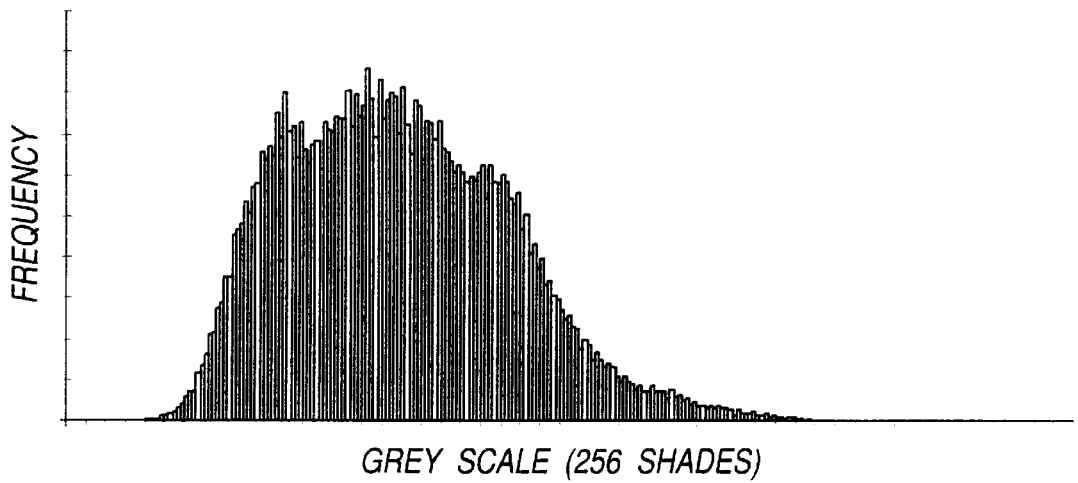
FIG. 15 illustrates a histogram of intensity as a function of shade of grey corresponding to the image of FIG. 13.
Figure 16:
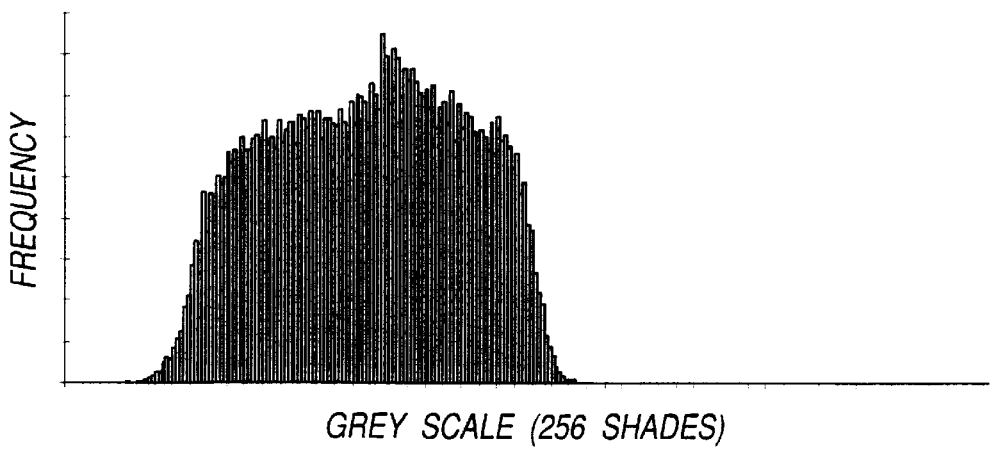
FIG. 16 illustrates a histogram of intensity as a function of shade of grey corresponding to the image of FIG. 14.

The device further comprises an analysing unit 61 which comprises processing means (not illustrated) for operating on the signals received from the one or more detectors 29 to extract relevant information as signals. The extracted signals can be provided to a display (not illustrated) for displaying one or more two-dimensional images which are in part representative of the three-dimensional distribution of one or more components in a sample 3, such as an active ingredient or an excipient in a pharmaceutical sample. By way of example, FIGS. 11 and 12 illustrate respectively images generated from radiation transmitted through first and second oppositely-directed surfaces 3a, 3b of a first sample 3 which includes a uniformly distributed component in a carrier matrix and FIGS. 13 and 14 illustrate respectively images generated from radiation transmitted through first and second oppositely-directed surfaces 3a, 3b of a second sample 3 which includes a non-uniformly distributed component in a carrier matrix (with the component being confined to a thickness adjacent the first surface 3a of the sample 3). In these images the lighter or more intense regions are representative of the component. As will be apparent to the naked eye, the image in FIG. 14, which is of radiation transmitted through the second surface 3b of the second sample 3, includes no discrete light regions and is representative of no component being present adjacent the second surface 3b of the sample 3. Indeed, FIGS. 13 and 14 manifestly evidence that to determine the three-dimensional distribution of a component in a sample it is not sufficient to image radiation transmitted in a single direction through a sample. The extracted signals are then converted to respective grey scale vectors which are mathematically representative of the extracted signals and provide for the generation of, for example, histograms which are representative of intensity as a function of the grey scale. In the images of FIGS. 11 to 14, each image is an 8-bit image, is but it will be understood that for enhanced resolution each image could, for example, be a 24-bit image. By way of example, FIGS. 15 and 16 represent respectively histograms corresponding to the transmission images from the second sample 3 as illustrated in FIGS. 13 and 14. As a measure of the homogeneity of a sample 3, univariate or multivariate image analysis techniques can be applied to the histograms; principal component analysis, partial least squares analysis or neural network analysis being common multivariate image analysis techniques. Such a measure, when calibrated, can be correlated to the three-dimensional distribution of a component in a sample 3. These converted signals can then be provided to the manufacturing equipment of the sample 3 for process control, such as in the control of mixing systems and in sample sorting. In this preferred embodiment separate histograms are generated from single images generated from radiation transmitted through respective surfaces 3a, 3b of a sample 3. In one alternative embodiment the images generated from each transmission measurement could be merged and operated upon as in effect a single histogram. In another alternative embodiment histograms could be generated from a plurality of images generated from each transmission measurement, which histograms could then be operated upon separately or merged prior to being operated upon.

In a first mode of use, where the samples 3 are moving continuously through the track 7 of the sample positioning unit 1, the radiation generating unit 16 is actuated so as to irradiate each respective sample 3 when in a predetermined position in front thereof with radiation of a single frequency or frequency band or with radiation comprising a plurality of single frequencies or frequency bands. In a particularly preferred embodiment the radiation generating unit 16 is actuated on receiving a signal from a sensor (not illustrated) which confirms the predetermined position of the respective sample 3. At the same time, the detector unit 25 detects the images of radiation received from the sample 3 and the analysing unit 61 extracts as signals relevant information which is representative of the three-dimensional distribution of one or more components in the sample 3, which extracted signals are then converted and further utilised.

In a second mode of use, where the samples 3 are moved in stepwise manner through the track 7 of the sample positioning unit 1, the radiation generating unit 16 is actuated so as to irradiate each respective sample 3 when stationary in a predetermined position in front thereof with radiation of a single frequency or frequency band or with radiation comprising a plurality of single frequencies or frequency bands. Otherwise, the device operates as in the above-described first mode.

In the above-described preferred embodiment the radiation generating unit 16 is configured to irradiate substantially the entire area of each of the first and second surfaces 3a, 3b of the sample 3 and the at least one detector 29 in the detector unit 25, in being a two-dimensional array detector, captures the entire sample image at the same instant. It will be appreciated, however, that other configurations are possible.

Figure 17:
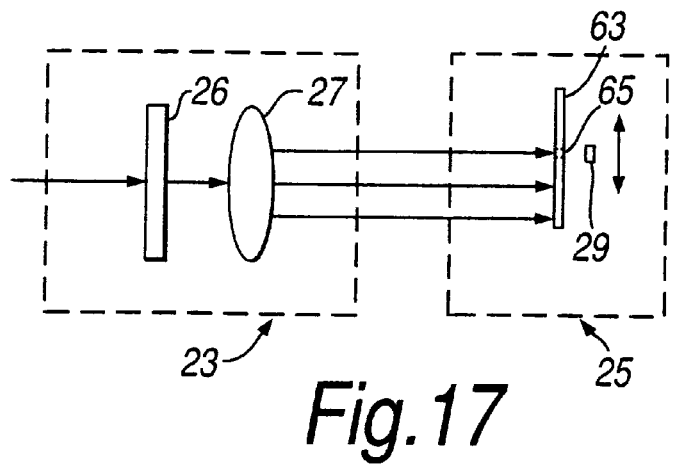
FIG. 17 illustrates schematically an alternative detector unit for the device of FIG. 1.

In one modification, as illustrated in FIG. 17, the device comprises the same radiation generating unit 16 as in the above-described preferred embodiment, but instead of being a two-dimensional array detector the at least one detector 29 is a one-dimensional array detector, particularly a CMOS chip, a CCD chip or a focal plane array, which is of sufficient length to capture the sample image in one direction and is moved in the orthogonal direction to capture the entire sample image on a time resolved basis. In this embodiment the detector unit 25 includes a plate 63 which includes a narrow slit 65 that extends in the one direction through which radiation in use passes and behind which the at least one detector 29 is disposed, with the at least one detector 29 and the plate 63 being moved together in unison in the orthogonal direction so as to capture the entire sample image on a time resolved basis.

Figure 18:
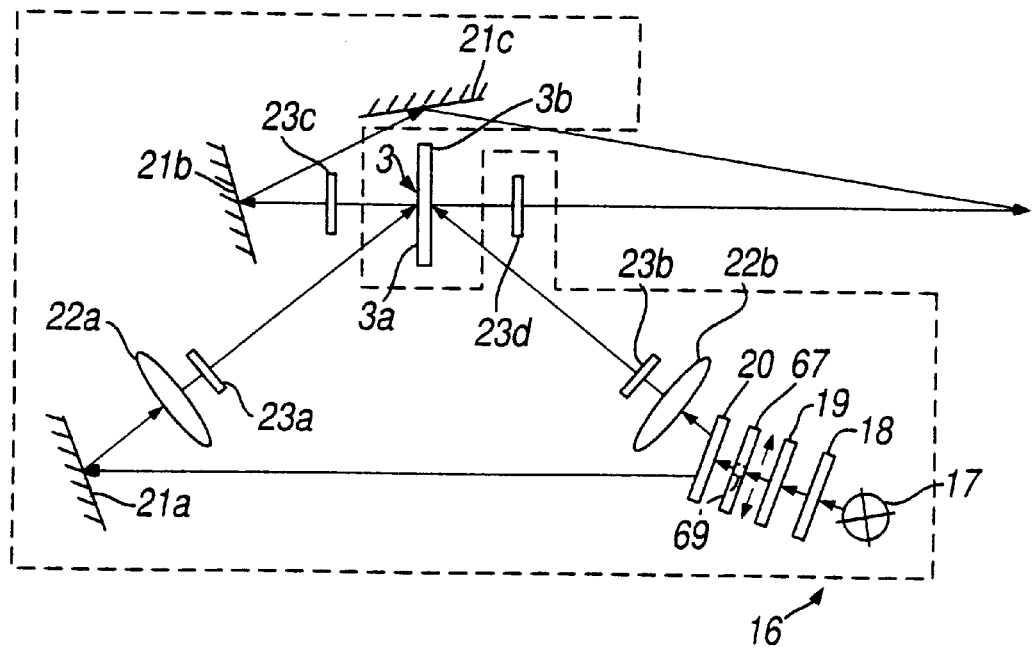
FIG. 18 illustrates schematically an alternative radiation generating unit for the device of FIG. 1.

In another modification, as illustrated in FIG. 18, the device comprises the same detector unit 25 as in the above-described preferred embodiment, but instead of the radiation generating unit 16 being configured uniformly to irradiate substantially entirely the first and second surfaces 3a, 3b of the sample 3, the radiation generating unit 16 is configured to generate a line of radiation in one direction which is in use scanned in the orthogonal direction over the respective surfaces 3a, 3b of the sample 3. In this embodiment the radiation generating unit 16 includes upstream of the beam splitter 20 a plate 67 which includes a narrow slit 69 that extends in the one direction through which radiation is in use provided, which plate 67 is in use moved in the orthogonal direction so as to scan substantially the entire area of the respective surfaces 3a, 3b of the sample 3 with the line of radiation. In this embodiment the at least one detector 29 in the detector unit 25 can comprise either a one or two-dimensional array detector. Where the at least one detector 29 is a one-dimensional array detector, the detector unit 25 has the same configuration as the above-described first modification and the plate 63 in the detector unit 25 is in use moved in the orthogonal direction in unison together with the plate 67 in the radiation generating unit 16 so as to capture the entire sample image on a time resolved basis.

Figure 19:
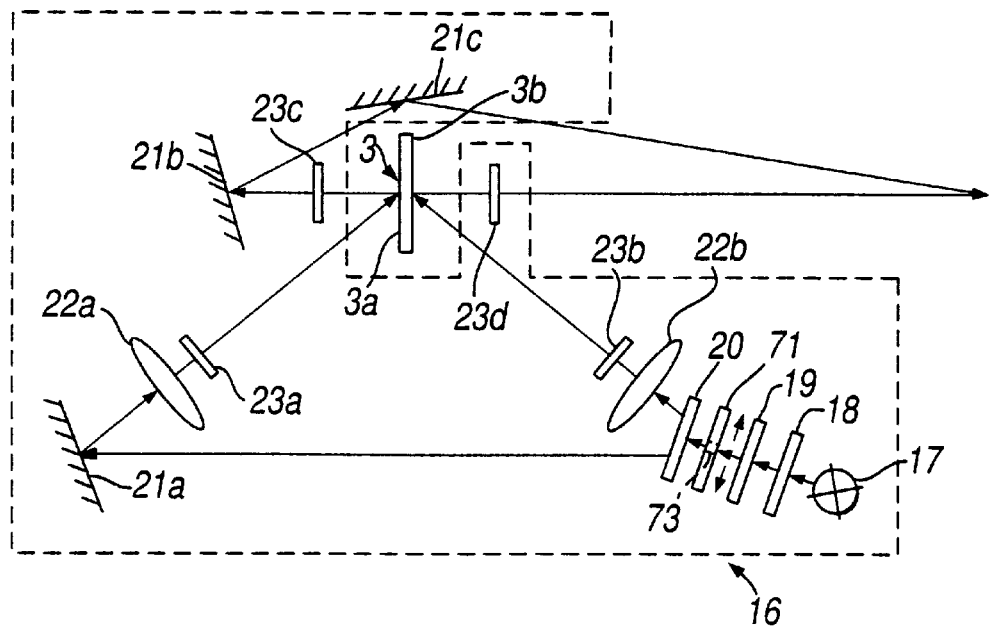
FIG. 19 illustrates schematically another alternative radiation generating unit for the device of FIG. 1.

In a further modification, as illustrated in FIG. 19, the device comprises the same detector unit 25 as in the above-described preferred embodiment, but instead of the radiation generating unit 16 being configured to irradiate uniformly substantially entirely the first and second surfaces 3a, 3b of the sample 3, the radiation generating unit 16 is configured to generate a line of radiation in one direction. In this embodiment the track 7 of the sample positioning unit 1 is configured such that each sample 3 moves therethrough relative to the line of radiation. In this way, the entire area of the respective surfaces 3a, 3b of the sample 3 is substantially scanned with the line of radiation. In this embodiment the radiation generating unit 16 includes a plate 71 disposed upstream of the beam splitter 20 which includes a narrow slit 73 that extends in the one direction through which radiation is in use provided. In this way, the entire sample image is captured on a time resolved basis as the sample 3 is moved through the track 7 of the sample positioning unit 1 relative to the line of radiation passing through the slit 73 in the plate 71. In this embodiment the at least one detector 29 in the detector unit 25 can comprise either a one or two-dimensional array detector. Where the at least one detector 29 is a one-dimensional array detector, the detector unit 25 has the same configuration as in the above-described first modification but the plate 63 and the at least one detector 29 in the detector unit 25 are fixed in position such that the slit 65 in the plate 63 and the at least one detector 29 in the detector unit 25 are in alignment with the slit 73 in the plate 71 in the radiation generating unit 16.

Figure 20:
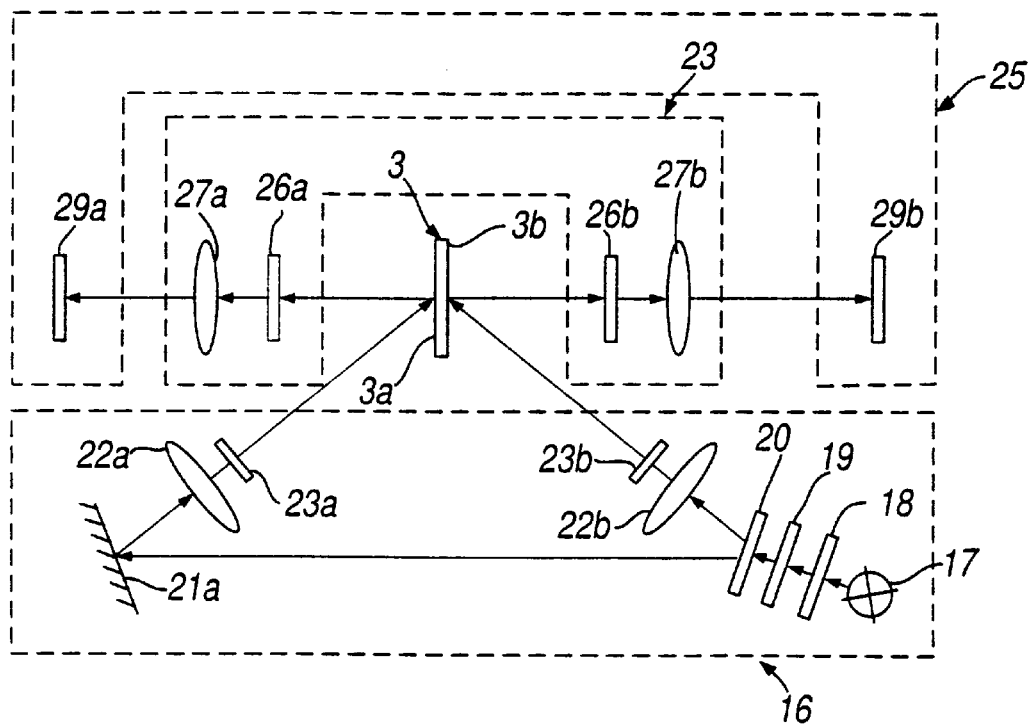
FIG. 20 illustrates schematically a further alternative radiation generating unit, an alternative imaging unit and an alternative detector unit for the device of FIG. 1.

In the above-described preferred embodiment the radiation generating unit 16 is configured to provide the radiation from the sample 3 commonly to the imaging unit 23. As illustrated in FIG. 20, in one modification the radiation generating unit 16 is configured, by omitting the second and third mirrors 21b, 21c and the third and fourth shield plates 23c, 23d, to provide separately both the radiation transmitted through the sample 3 in the direction from the second surface 3b to the first surface 3a and the radiation reflected from the first surface 3a of the sample 3 and both the radiation transmitted through the sample 3 in the direction from the first surface 3a to the second surface 3b and the radiation reflected from the second surface 3b of the sample 3. Correspondingly, the imaging unit 23 comprises a first polarizer 26a and at least one first optical element 27a, in this embodiment at least one lens, for receiving both radiation transmitted through the sample 3 in the direction from the second surface 3b to the first surface 3a and radiation reflected from the first surface 3a of the sample 3 and a second polarizer 26b and at least one second optical element 27b, again in this embodiment at least one lens, for receiving both radiation transmitted through the sample 3 in the direction from the first surface 3a to the second surface 3b and radiation reflected from the second surface 3b of the sample 3, and the detector unit 25 comprises at least one first detector 29a for receiving the radiation imaged by the at least one first lens 27a and at least one second detector 29b for receiving the radiation imaged by the at least one second lens 27b. In a first configuration, the at least one radiation source 17 via the beam splitter 20 and the first mirror 21 a provides radiation to the first surface 3a of the sample 3, with radiation being prevented from passing to the second surface 3b of the sample 3 by the second shield plate 23b. In this way, the at least one first detector 29a in the detector unit 25 is provided with an image of radiation reflected from the first surface 3a of the sample 3 and the at least one second detector 29b in the detector unit 25 is provided with an image of radiation transmitted through the sample 3 in the direction from the first surface 3a to the second surface 3b. In a second configuration, the at least one radiation source 17 provides radiation via the beam splitter 20 to the second surface 3b of the sample 3, with radiation being prevented from passing to the first surface 3a of the sample 3 by the first shield plate 23a. In this way, the at least one first detector 29a in the detector unit 25 is provided with an image of radiation transmitted through the sample 3 in the direction from the second surface 3b to the first surface 3a and the at least one second detector 29b in the detector unit 25 is provided with an image of radiation reflected from the second surface 3b of the sample 3. In use, radiation is provided selectively, preferably simultaneously or alternately, to the first and second surfaces 3a, 3b of the sample 3 in order for the detector unit 25 to capture the respective transmission and reflectance images.

Figure 21:
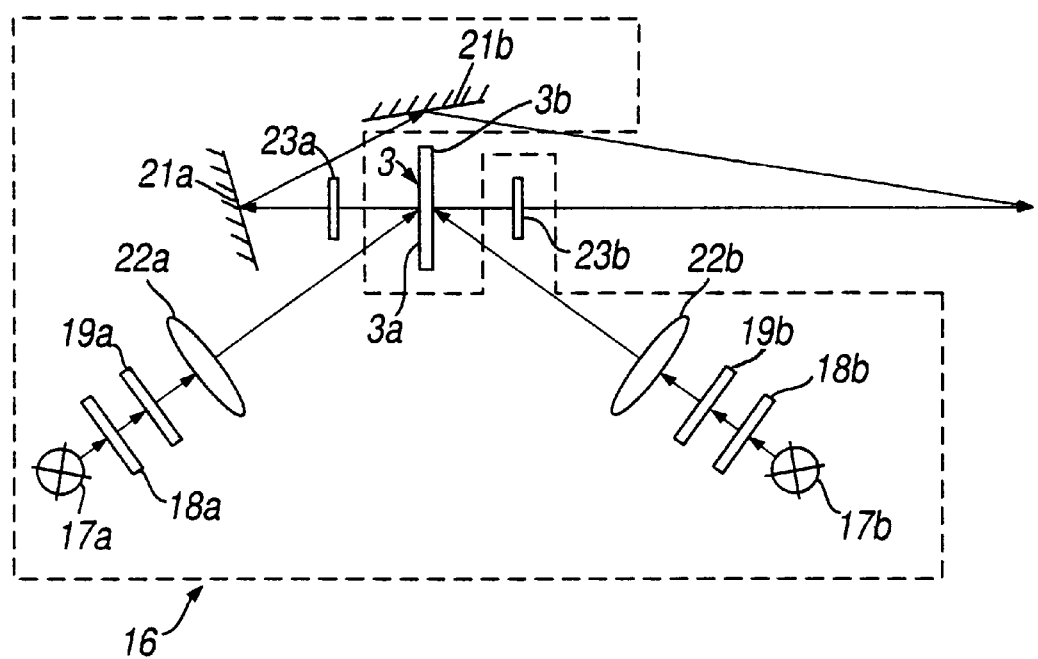
FIG. 21 illustrates schematically a yet further alternative radiation generating unit for the device of FIG. 1.

In the above-described preferred embodiment the radiation generating unit 16 is configured such that the at least one radiation source 17 provides radiation both to the first and second surfaces 3a, 3b of the sample 3. In a modification, as illustrated in FIG. 21, the radiation generating unit 16 comprises at least one first radiation source 17a which is configured to provide radiation to the first surface 3a of the sample 3 for taking a transmission measurement from the sample 3 in the direction from the first surface 3a to the second surface 3b of the sample 3 and a reflectance measurement from the first surface 3a of the sample 3 and at least one second radiation source 17b which is configured to provide radiation to the second surface 3b of the sample 3 for taking a transmission measurement from the sample 3 in the direction from the second surface 3b to the first surface 3a of the sample 3 and a reflectance measurement from the second surface 3b of the sample 3. The radiation generating unit 16 further comprises a plurality of optical elements 18a, 18b, 19a, 19b, 21a, 21b, 22a, 22b, 23a, 23b, which include first and second polarizers 18a, 18b, first and second diffusers 19a, 19b, first and second mirrors 21a, 21b, first and second lenses 22a, 22b and first and second shield plates 23a, 23b, that allow transmission measurements to be taken in both directions through the sample 3 and reflectance measurements to be taken from both surfaces 3a, 3b of the sample 3. As will be described hereinbelow, the at least one first radiation source 17a, the at least one second radiation source 17b, the first and second mirrors 21a, 21b and the first and second shield plates 23a, 23b are operably configured for the detector unit 25 to capture the respective transmission and reflectance images. In a first configuration, the at least one second radiation source 17b provides no radiation to the second surface 3b of the sample 3 and the at least one first radiation source 17a provides radiation to the first surface 3a of the sample 3, with the radiation reflected by the first surface 3a of the sample 3 being blocked by the first shield plate 23a. In this way, the detector unit 25 is provided with an image of radiation transmitted through the sample 3 in the direction from the first surface 3a to the second surface 3b. In a second configuration, the at least one second radiation source 17b provides no radiation to the second surface 3b of the sample 3 and the at least one first radiation source 17a provides radiation to the first surface 3a of the sample 3, with the radiation transmitted through the sample 3 in the direction from the first surface 3a to the second surface 3b being blocked by the second shield plate 23b. In this way, the detector unit 25 is provided via the first and second mirrors 21a, 21b with an image of radiation reflected from the first surface 3a of the sample 3. In a third configuration, the at least one first radiation source 17a provides no radiation to the first surface 3a of the sample 3 and the at least one second radiation source 17b provides radiation to the second surface 3b of the sample 3, with the radiation reflected from the second surface 3b of the sample 3 being blocked by the second shield plate 23b. In this way, the detector unit 25 is provided via the first and second mirrors 21a, 21b with an image of radiation transmitted through the sample 3 in the direction from the second surface 3b to the first surface 3a. In a fourth configuration, the at least one first radiation source 17a provides no radiation to the first surface 3a of the sample 3 and the at least one second radiation source 17b provides radiation to the second surface 3b of the sample 3, with the radiation transmitted through the sample 3 in the direction from the second surface 3b to the first surface 3a being blocked by the first shield plate 23a. In this way, the detector unit 25 is provided with an image of radiation reflected from the second surface 3b of the sample 3. In use, radiation is provided selectively, preferably simultaneously or alternately, to the first and second surfaces 3a, 3b of the sample 3 in order for the detector unit 25 to capture the respective transmission and reflectance images.

Finally, it will be understood that the present invention has been described in its preferred embodiment and can be modified in many different ways without departing from the scope of the invention as defined by the appended claims.

What is claimed is:

1. A device for analyzing a sample, comprising:
   a sample positioning unit for positioning a sample;
   a radiation generating unit for providing a first beam of electromagnetic radiation to a first surface of the sample and a second beam of electromagnetic radiation to a second surface of the sample;

an imaging unit for providing at least one image from radiation transmitted through each of the first and second surfaces of the sample;

a detector unit for capturing the images provided by the imaging unit and generating signals corresponding thereto; and an analyzing unit for operating on the signals received from the detector unit and generating signals representative of the three-dimensional distribution of at least one component in the sample.

2. The device according to claim 1, wherein the sample positioning unit comprises a track through which the samples are moved.

3. The device according to claim 2, wherein the sample positioning unit is configured such that samples are moved in a stepwise manner through the track.

4. The device according to claim 2, wherein the sample positioning unit is configured such that samples are moved continuously through the track.

5. The device according to claim 1, wherein at least one of the beams of radiation is collimated.

6. The device according to claim 1, wherein at least one of the beams of radiation is converging.

7. The device according to claim 1, wherein at least one of the beams of radiation is diverging.

8. The device according to claim 1, wherein the principal axis of at least one of the beams of radiation is substantially normal to the respective surface of the sample.

9. The device according to claim 1, wherein the principal axis of at least one of the beams of radiation is at an angle to the respective surface of the sample.

10. The device according to claim 1, wherein at least one of the beams of radiation is dimensioned to irradiate substantially entirely the respective surface of the sample.

11. The device according to claim 1, wherein at least one of the beams of radiation is dimensioned to irradiate an area smaller than that of the respective surface of the sample.

12. The device according to claim 1, wherein the radiation generating unit is configured so as in use to move at least one of the beams of radiation in at least one direction and thereby scan the beam of radiation over substantially entirely the respective surface of the sample.

13. The device according to claim 1, wherein the first and second surfaces of the sample are oppositely-directed surfaces.

14. The device according to claims 1, wherein at least one of the beams of radiation is visible light.

15. The device according to claims 1, wherein at least one of the beams of radiation is infra-red radiation.

16. The device according to claim 15, wherein the infra-red radiation is in the near infrared region.

17. The device according to claim 16, wherein the infra-red radiation has a frequency in the range corresponding to wavelengths of from 700 to 1700 nm.

18. The device according to claim 1, wherein at least one of the beams of radiation is x-ray radiation.

19. The device according to claim 1, wherein the radiation generating unit comprises at least one radiation source and at least one optical element.

20. The device according to claim 19, wherein the radiation generating unit further comprises a moving diffuser downstream of each radiation source.

21. The device according to claim 19 or 20, wherein the radiation generating unit further comprises at least one polarizer downstream of each radiation source.

22. The device according to claim 19, wherein the radiation generating unit comprises a first radiation source, a second radiation source and associated optical elements, each of the radiation sources providing at least one beam of radiation for irradiating respectively the first and second surfaces of the sample.

23. The device according to claim 19, wherein any or each of the radiation sources comprises a laser.

24. The device according to claim 19, wherein any or each of the radiation sources comprises a light-emitting diode.

25. The device according to claim 1, wherein the imaging unit comprises at least one optical element for providing al least one image of radiation transmitted through each of the first and second surfaces of the sample.

26. The device according to claim 25, wherein the imaging unit further comprises at least one polarizer for polarizing radiation transmitted through each of the first and second surfaces of the sample.

27. The device according to claim 25 or 26, wherein the imaging unit further comprises at least one beam splitter for providing a plurality of images of different single frequency or frequency band from radiation transmitted through each of the first and second surfaces of the sample.

28. The device according to claim 27, wherein the beam splitter comprises a frequency dependent beam splitter, which together with at least one optical element provides a plurality of images of different single frequency or frequency band from radiation transmitted through each of the first and second surfaces of the sample.

29. The device according to claim 27, wherein the beam splitter comprises a non-frequency dependent beam splitter, which separates radiation transmitted through each of the first and second surfaces of the sample into a plurality of components, and a plurality of filters for filtering each of the respective components to provide radiation of different single frequency or frequency band, the beam splitter and the filters together with at least one optical element providing a plurality of images of different single frequency or frequency band from radiation transmitted through each of the first and second surfaces of the sample.

30. The device according to claim 27, wherein the beam splitter comprises a transmission grating, which together with at least one optical element provides a plurality of images of different single frequency or frequency band from radiation transmitted through each of the first and second surfaces of the sample.

31. The device according to claim 27, wherein the beam splitter comprises a prism array, which separates radiation transmitted through each of the first and second surfaces of the sample into a plurality of components, and a plurality of filters for filtering each of the respective components to provide radiation of different single frequency or frequency band, the prism array and the filters together with at least one optical element providing a plurality of images of different single frequency or frequency band from radiation transmitted through each of the first and second surfaces of the sample.

32. The device according to claim 27, wherein the beam splitter comprises a plurality of lenses, which separate radiation transmitted through each of the first and second surfaces of the sample into a plurality of components, and a plurality of filters for filtering each of the respective components to provide radiation of different single frequency or frequency band, the lenses and the filters together with at least one optical element providing a plurality of images of different single frequency or frequency band from radiation transmitted through each of the first and second surfaces of the sample.

33. The device according to claim 1, wherein the detector unit comprises at least one detector.

34. The device according to claim 33, comprising a single detector.

35. The device according to claim 33, comprising a plurality of detectors.

36. The device according to claim 34, wherein the detector is a two-dimensional array detector.

37. The device according to claim 35, wherein each detector is a sub-array of an array detector.

38. The device according to claim 34, wherein the detector is a one-dimensional array detector.

39. The device according to claim 33, wherein the detector unit is configured such that in use at least one detector is moved to capture the images provided by the imaging unit.

40. The device according claim 33, wherein at least one detector comprises any of a CMOS chip, a CCD chip or a focal plane array.

41. A method of analyzing a sample, comprising the steps of:

providing a sample;

irradiating a first surface of the sample with a first beam of electromagnetic radiation and irradiating a second surface of the sample with a second beam of electromagnetic radiation;

imaging radiation transmitted through the first and second surfaces of the sample;

capturing the imaged radiation and generating signals corresponding thereto; and operating on the signals corresponding to the imaged radiation and generating signals representative of the three-dimensional distribution of at least one component in the sample.

42. The method according to claim 41, wherein the sample is stationary during irradiation.

43. The method according to claim 41, wherein the sample is moving during irradiation.

44. The method according to any of claims 41 to 43, wherein at least one of the beams of radiation is collimated.

45. The method according to any of claims 41 to 43, wherein at least one of the beams of radiation is converging.

46. The method according to any of claims 41 to 43, wherein at least one of the beams of radiation is diverging.

47. The method according to claim 41, wherein the principal axis of at least one of the beams of radiation is substantially normal to the respective surface of the sample.

48. The method according to claim 41 wherein the principal axis of at least one of the beams of radiation is at an angle to the respective surface of the sample.

49. The method according to claim 41, wherein at least one of the beams of radiation is dimensioned to irradiate substantially entirely the respective surface of the sample.

50. The method according to claim 41, wherein at least one of the beams of radiation is dimensioned to irradiate an area smaller than that of the respective surface of the sample and the respective surface of the sample is irradiated substantially entirely by scanning the at least one of the beams of radiation thereover.

51. The method according to claim 41, wherein at least one of the beams of radiation is dimensioned to irradiate an area smaller than that of the respective surface of the sample and the respective surface of the sample is irradiated substantially entirely by moving the sample so as to scan at least one of the beams of radiation thereover.

52. The method according to claim 50 or 51, wherein at least one of the beams of radiation is in the form of a line.

53. The method according, to claim 41, wherein the first and second surfaces of the sample are oppositely-directed surfaces.

54. The method according to claim 41, wherein the radiation comprises a single frequency, a single frequency band, a plurality of single frequencies or a plurality of frequency bands.

55. The method according to claim 41, wherein at least one of the beams of radiation is continuous.

56. The method according to claim 41, wherein at least one of the beams of radiation is pulsed.

57. The method according to claim 56, wherein the frequency or frequency band of the radiation in each pulse is different.

58. The method according to claim 41, wherein at least one of the beams of radiation is visible light.

59. The method according to claim 41, wherein at least one of the beams of radiation is infra-red radiation.

60. The method according to claim 59, wherein the infra-red radiation is in the near infra-red region.

61. The method according to claim 60, wherein the infra-red radiation has a frequency in the range corresponding to wavelengths of from 700 to 1700 nm.

62. The method according to claim 41, wherein at least one of the beams of radiation is x-ray radiation.

63. The method according to claim 41, wherein the step of imaging radiation comprises the step of providing a plurality of images of different single frequency or frequency band from radiation transmitted through each of the first and second surfaces of the sample.

64. The device according to claim 35, wherein at least one detector is a two-dimensional array detector.

65. The device according to claim 35, wherein at least one detector is a one-dimensional array detector.

* * * * *